(12) United States Patent  
Huttner

(10) Patent No.: US 9,114,202 B1  
(45) Date of Patent: Aug. 25, 2015

(54) LIGHTED SUCTION DEVICE

(71) Applicant: Bionix Development Corporation, Toledo, OH (US)

(72) Inventor: James J. Huttner, Sylvania, OH (US)

(73) Assignee: Bionix Development Corporation, Toledo, OH (US)

( * ) Notice: Subject to any disclaimer, the term of this patent is extended or adjusted under 35 U.S.C. 154(b) by 132 days.

(21) Appl. No.: 13/677,393

(22) Filed: Nov. 15, 2012

Related U.S. Application Data

(60) Provisional application No. 61/560,023, filed on Nov. 15, 2011.

(51) Int. Cl.
*A61B 1/06* (2006.01)
*A61M 1/00* (2006.01)
*A61B 1/018* (2006.01)

(52) U.S. Cl.
CPC .............. *A61M 1/0039* (2013.01); *A61B 1/018* (2013.01); *A61B 1/06* (2013.01)

(58) Field of Classification Search
CPC .................... A61B 1/06–1/07; A61B 19/5202; A61B 2019/5206; A61B 2019/521
USPC ............ 600/184–249; 604/35, 118–121, 131; 606/107, 169
See application file for complete search history.

(56) References Cited

U.S. PATENT DOCUMENTS

| 3,261,356 | A  | * | 7/1966 | Wallace ........................ 604/264 |
|-----------|----|---|--------|-----------------------------------------|
| 5,897,489 | A  | * | 4/1999 | Urbanowicz et al. ......... 600/185 |
| 6,569,089 | B1 | * | 5/2003 | Covington et al. ............ 600/199 |
| 7,641,644 | B2 | * | 1/2010 | Chang et al. .................. 604/500 |
| 2004/0195975 | A1 | * | 10/2004 | Fregoso ......................... 315/219 |
| 2005/0171408 | A1 | * | 8/2005 | Parker ............................ 600/249 |
| 2006/0276693 | A1 | * | 12/2006 | Pacey ............................ 600/188 |
| 2007/0060793 | A1 | * | 3/2007 | DeGould ....................... 600/201 |
| 2007/0088203 | A1 | * | 4/2007 | Lau ............................... 600/205 |
| 2008/0146878 | A1 | * | 6/2008 | Frost et al. .................... 600/188 |
| 2009/0253967 | A1 | * | 10/2009 | Gill et al. ...................... 600/249 |
| 2009/0312783 | A1 | * | 12/2009 | Whayne et al. ............... 606/190 |
| 2010/0249528 | A1 | * | 9/2010 | Vayser et al. ................. 600/245 |
| 2011/0112376 | A1 | * | 5/2011 | Vayser et al. ................. 600/249 |
| 2011/0313412 | A1 | * | 12/2011 | Kim et al. ...................... 606/33 |
| 2012/0179187 | A1 | * | 7/2012 | Loushin et al. ............... 606/185 |
| 2012/0277537 | A1 | * | 11/2012 | Kucklick et al. .............. 600/203 |
| 2013/0012783 | A1 | * | 1/2013 | Vayser et al. ................. 600/249 |
| 2013/0012784 | A1 | * | 1/2013 | Vayser et al. ................. 600/249 |

* cited by examiner

*Primary Examiner* — Eduardo C Robert
*Assistant Examiner* — Michelle C Eckman
(74) *Attorney, Agent, or Firm* — Marshall & Melhorn, LLC

(57) ABSTRACT

A lighted suction device comprises a light pipe member extending from a proximal end to a tip so as to allow light to travel down the light pipe member from the proximal end to the tip, and a suction channel integral to the light pipe member or a suction catheter member that is affixed to the light pipe member having an opening at the tip of the light pipe member and a connector at its proximal end for connection to a source of vacuum. The tip of the light pipe member is introduced into a body orifice, suction is applied wax, debris, a foreign object, or the like in the body orifice, and the light pipe member is withdrawn to remove the wax, debris, and/or foreign object.

13 Claims, 4 Drawing Sheets

LIGHTED SUCTION DEVICE

RELATED APPLICATION

This application is claiming the benefit, under 35 U.S.C. §119(e), of the provisional application filed Nov. 15, 2011 under 35 U.S.C. §111(b), which was granted Ser. No. 61/560,023. This provisional application is hereby incorporated by reference in its entirety.

BACKGROUND OF THE INVENTION

Cerumen impaction remains a significant medical problem. Over 14 million visits are made to physicians every year, many for complaints associated with ear wax impaction. Cerumen impaction can cause hearing loss, tinnitus, pain, infection, and can seriously impair the functioning of hearing aids and tympanostomy tubes. Cerumen impaction is particularly prevalent in the elderly population. This group is more likely to produce hard, dry wax that adheres to the ear canal wall. They are also the group most likely to use hearing aids that impede the natural progression of wax from the ear canal.

There are a variety of techniques available to remove impacted ear wax from the ear canal. Both curettage and irrigation are well known and frequently used procedures that effectively remove ear wax. Another procedure widely used for cerumen removal is suction. This method is particularly effective when the ear wax has a soft, cheese-like consistency. Ear suction is also effective when the ear wax has been treated with a ceruminolytic agent to soften and loosen it, leaving a gooey mess in the ear canal that must be removed to obtain an adequate examination of the tympanic membrane. Suction is also a desirable technique in cases of active infection or with patent tympanostomy tubes, where pus and debris in the ear canal blocks adequate visualization of the ear drum and where irrigation is contraindicated and curettage may be ineffective.

Another cause for ear canal impaction is obstruction with a foreign object. Removal of foreign bodies, as they are called, are well known causes of emergency room and doctor's office visits. It is a particular problem in the pediatric age group, but is not limited to children. The types of foreign bodies found in ear canals range from beads and small toys, to cotton swab tips (from attempts at self-cleaning) and insects. Many of these objects are removed by grasping them with forceps, but round, smooth objects (e.g. beads, stones, toys) are best removed by ear suction.

Currently, ear suction is performed using a re-usable metal suction catheter. The suction catheter comprises a tube with an adaptor for mating with suction tubing, and a small regulating hole or slit that can be covered or uncovered by the user's thumb to break the vacuum as needed. The design of this suction catheter is similar to that of other suction catheters used for a variety of medical purposes. The only difference is that suction catheters used for the ear have a significantly smaller bore size, usually a 7 French or smaller, to accommodate the small diameter of the ear canal. Suction is provided by connection with a standard suction pump or central suction system (as found in hospitals).

One problem with the current ear suction techniques is that it is a "blind" procedure, in that it is difficult for the operator to visualize accurately the suction tip in the ear canal during the suctioning. ENT physicians typically use an operating microscope, or magnifying eye loupes and head-lamp to allow the procedure to be visualized. The current ear suction devices do not have either intrinsic illumination or visualization.

SUMMARY OF THE INVENTION

The lighted suction device of the invention comprises a light pipe member extending from a proximal end to a tip that is composed of a transparent material with low haze so as to allow light to travel down the light pipe member from the proximal end to the tip, and a suction channel integral to the light pipe member or a suction catheter member that is affixed in a permanent fashion to the light pipe member having an opening at the tip of the light pipe member and a connector at its proximal end for connection to a source of vacuum.

According to the method of the invention, a light source is selectively connected to the proximal end of the light pipe member, and a source of vacuum is selectively connected to the connector of the suction channel or suction catheter member. The tip of the light pipe member is introduced into a body orifice, suction is applied wax, debris, a foreign object, or the like in the body orifice, and the light pipe member is withdrawn to remove the wax, debris, and/or foreign object.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

Figure 1:
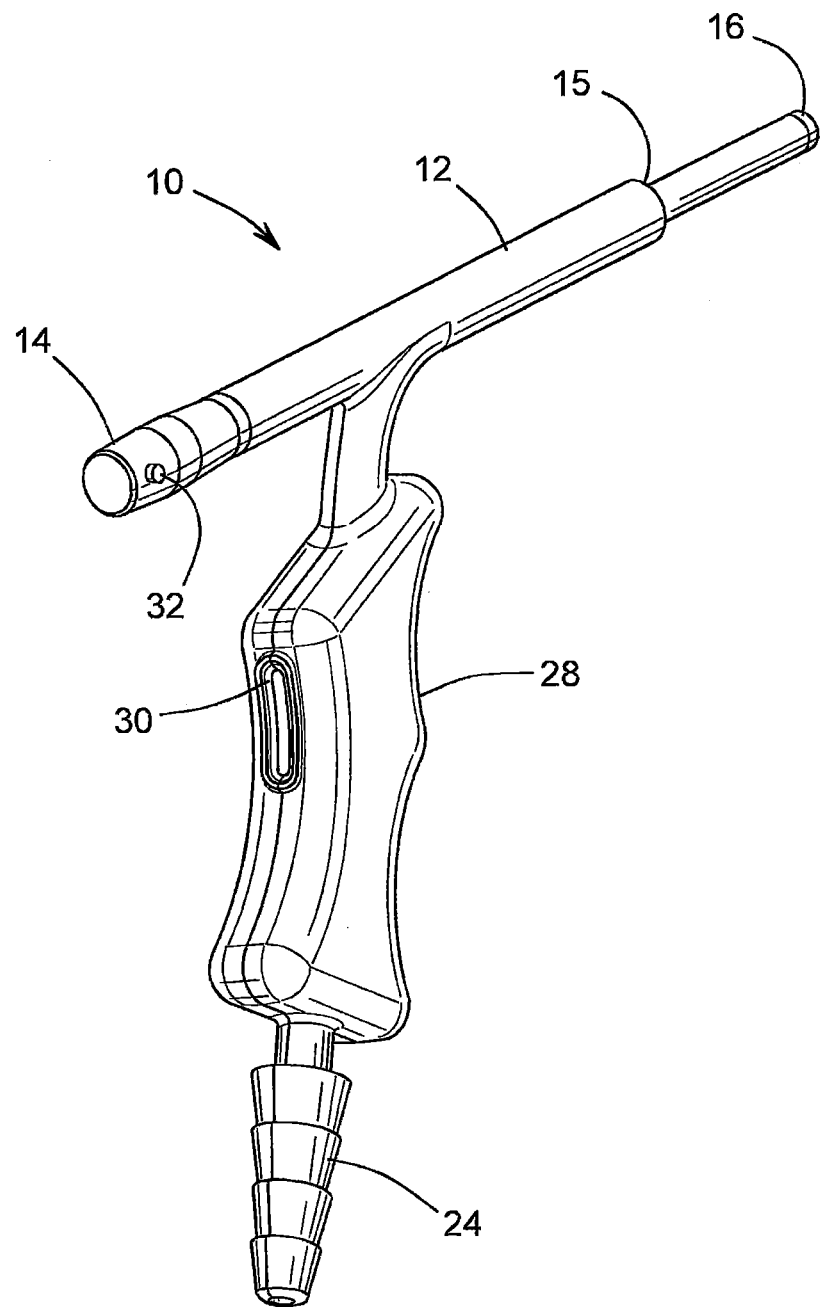
FIG. 1 is a perspective view of a preferred embodiment of the lighted suction device of the invention.

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

The current invention is a lighted suction device and method of removing an object from a body orifice such as the ear canal utilizing the lighted suction device to provide both illumination and visualization during the procedure. The illumination is preferably provided by a white LED (light emitting diode) that transmits light into the ear canal using the suction device as a light pipe. The visualization may be enhanced by a magnifying lens that can be removably attached to the suction device. The lighted suction device assembly may be attached to a standard vacuum unit as described below to provide suction for the procedure.

Referring to the drawings, the lighted suction device 10 includes a light pipe member or portion 12. The light pipe member 12 is elongate, extending from a butt or proximal end 14 to a shoulder 15 to a tip 16. It may be preferred to form the tip 16 of the lighted suction device 10 so as to be slightly flared, to allow it to more readily adhere to round foreign bodies. The proximal end 14 of the light pipe member 12 is designed to connect to a light source 18, preferably a bright white LED light source that provides the source of illumination. At least the light pipe member 12 of the lighted suction device 10 is composed of a transparent material that has good transparency and haze that is sufficiently low to allow it to function as a light pipe. The transparent material of the light pipe member 12 may be glass or a plastic material, preferably a polycarbonate, acrylic or co-polyester material.

Figure 2:
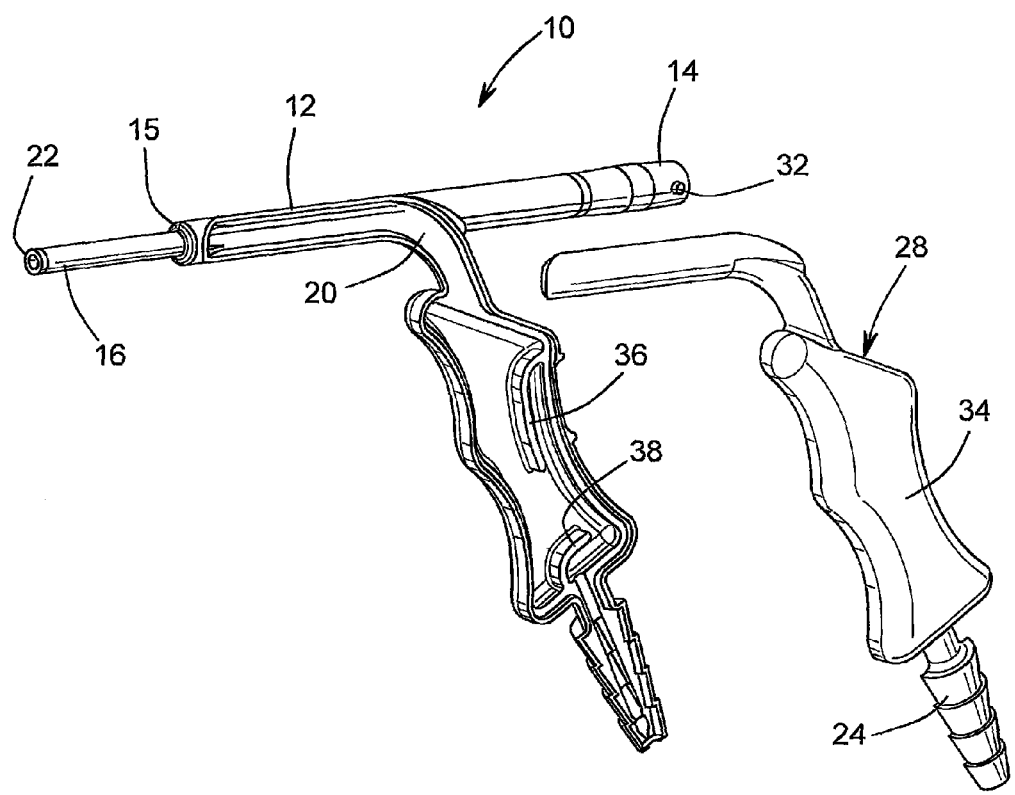
FIG. 2 is a perspective, exploded view of the device shown in FIG. 1.

The lighted suction device 10 further includes a suction channel or passage 20 that may be integral to the light pipe member 12 or may be a catheter-type member that is affixed in a permanent fashion to the light pipe member 12. In the illustrated embodiment, the suction channel 20 is formed integrally with the light pipe member 12, as best seen in FIG. 2. The suction channel 20 terminates at one end in an opening 22 at the tip 16 of the light pipe member 12 and at the other end or proximal end in a connector 24 for connection to a source of vacuum 26.

The lighted suction device 10 preferably includes a handle 28 extending from the light pipe member 12. In the preferred, illustrated embodiment, a portion of the suction channel 20 and the connector 24 are formed integrally with the handle 28. The connector 28 is preferably a standard hose connector, such as the hose barb shown, allowing the lighted suction device 10 to connect with the suction channel 20 in fluid communication with any standard suction system, including a wall-vacuum or vacuum pump. A small hole 30 may preferably be located in the handle 28 of the lighted suction device 10 to allow finger-tip control of the vacuum by a user.

As can be seen in FIGS. 1 and 2, in a preferred embodiment the light pipe member 12, including the suction tip 16, and one half of the handle 28 and hose barb connector 24 are molded as a single piece, together forming a light pipe component assembly. The light pipe member 12 is connected to a LED light source 18 (shown schematically in FIG. 3) via the bayonette configuration 32 at its rearward or proximal end 14. Light travels from the light source 18 through the light pipe member 12, exiting as the light pipe member 12 transitions at the shoulder 15 to the tip 16 where it exceeds the critical angle. As shown, the handle portion 28 is formed from the assembly of the light pipe member 12 and the mating half 34 of the handle 28. Clearly seen is the thumb hole 30 for easy control of suction pressure. The interior of the handle 28 defines a portion of the suction channel 20, and preferably is provided with one or more baffles that form a debris trap for suctioned cerumen, objects or the like. FIG. 2 shows a first baffle 36 and a second baffle 38 within that portion of the suction channel 20 within the handle 28. The vacuum source 26 connects to the lighted suction device 10 via the hose barb connector 24 formed by the assembly of the light pipe component assembly and the mating half 34 of the handle 28.

In FIG. 2, an exploded view of the device 10, the interior geometry of the illustrated embodiment of the lighted suction device 10 is clearly visible. As shown, the single-piece light pipe component assembly of the lighted suction device 10 also includes the baffles 36 and 38 forming the debris trap. The suction tip 16 is shown as a closed channel at its distal end, transitioning into an open geometry that joins with the mating half 34 of the handle 28 and suction channel component of the device. As noted, the interior of the handle 28 has one or more baffles that serve to form a debris trap that catches larger particles and keeps them from being drawn into the suction tubing. The vacuum source 26 connects via suction tubing or the like to the hose barb connector 24 formed by the assembly of the light pipe component assembly and the mating half 34 of the handle 28.

Figure 3:
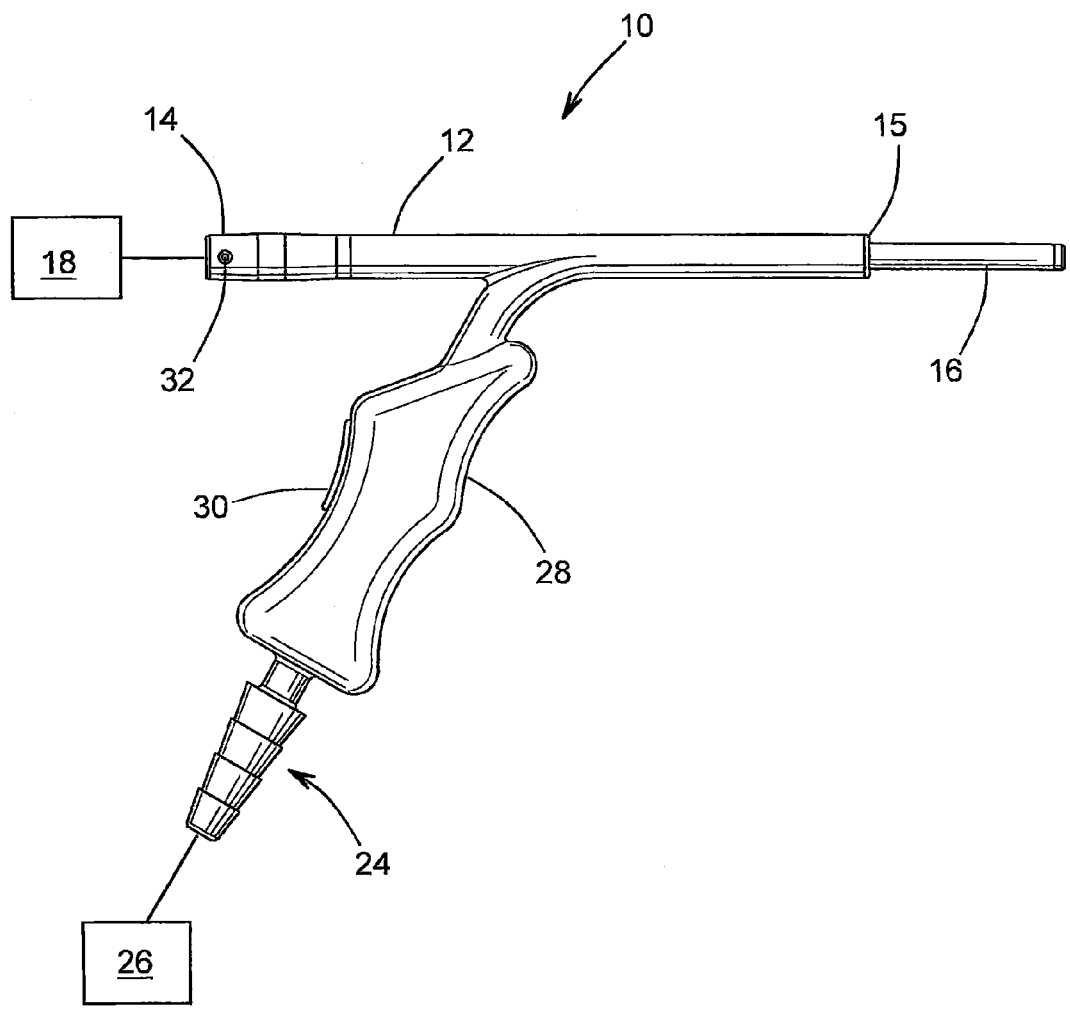
FIG. 3 is a side, partially schematic view of the device shown in FIG. 1.
Figure 4:
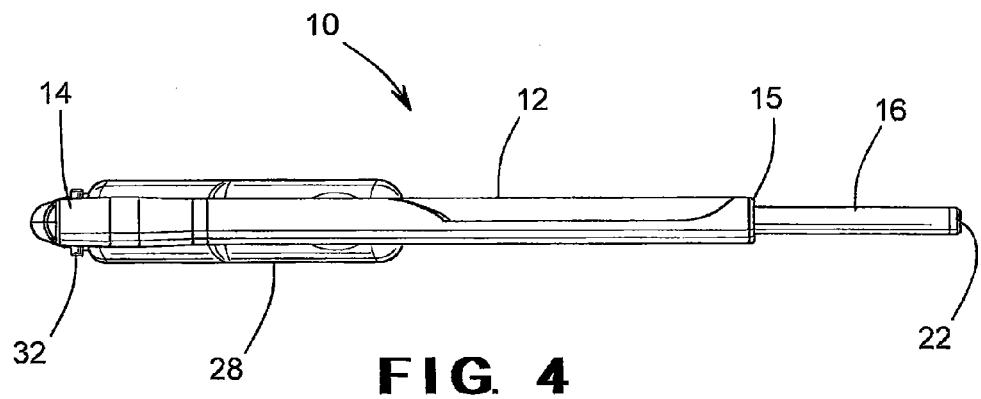
FIG. 4 is a top view of the device shown in FIG. 1.
Figure 5:
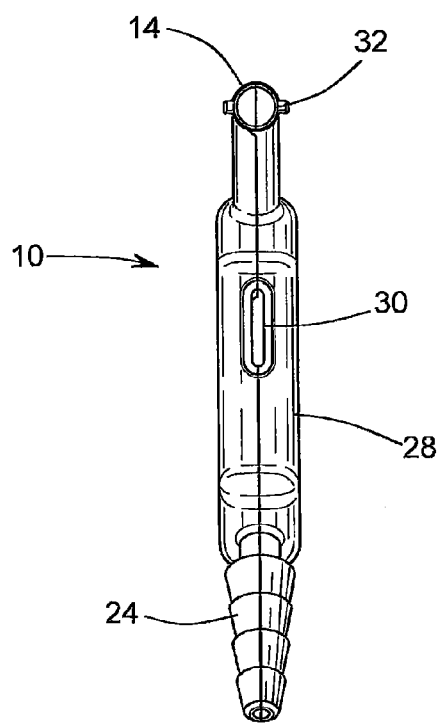
FIG. 5 is a rear view of the device shown in FIG. 1.

FIG. 3 shows a side view of the lighted suction device from 10 the perspective of the light pipe component assembly side, which as illustrated is molded as a single piece. The light pipe member 12 is shown from its rearward or proximal end 14, where it inserts into the LED light source 18, to the shoulder 15, where an abrupt transition to the suction tip 16 exceeds the critical angle for light transmission through the material, and thus allows light to escape (exit) at that point. The handle portion 28, containing the debris trap formed in the suction channel 20 by the baffles 36, 38 and the hose barb connector 24, extends downward and away from the light pipe member 12.

FIG. 7 shows the assembled lighted suction device 10 from the rear. In this view, the thumb hole 30 used to control the suction is clearly visible. Also, from this rear view it is evident how the two halves of the device mate to form the handle portion 28 and hose barb connector 30.

In accordance with the provisions of the patent statutes, the invention has been described in what is considered to represent its preferred embodiments. However, it should be noted that the invention could be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A lighted suction device comprising:
    a. a light pipe member extending from a proximal end to a shoulder to a tip, the light pipe member being composed of a transparent material with low haze so as to allow light to travel down the light pipe member from the proximal end toward the tip;
    b. a suction channel terminating at a distal end at an opening at the tip of the light pipe member and at a proximal end at a connector for connection to a source of vacuum; and
    c. a light source that removably connects to the proximal end of the light pipe member to allow light to transmit down the light pipe member and into a body orifice to provide illumination thereto;
        wherein the shoulder of the light pipe member is proximate the tip and has an abrupt transition that exceeds the critical angle for light transmission through the transparent material, such that light transmitted from the light source exits the light pipe member at the shoulder.

2. The lighted suction device of claim 1, further comprising a handle extending from the light pipe member, wherein the connector for the suction channel extends from the handle.

3. The lighted suction device of claim 2, the handle includes a hole in communication with the suction channel near the proximal end thereof that can be opened and closed by a user's thumb to control the suction at the distal end of the suction channel.

4. The lighted suction device of claim 2, wherein the handle includes one or more baffles within the suction channel to form a debris trap.

5. The lighted suction device of claim 1, further comprising a source of vacuum in communication with the connector of the suction channel.

6. The lighted suction device of claim 1, wherein the light source is a bright white light emitting diode (LED).

7. The lighted suction device of claim 1, wherein the transparent material is polycarbonate, acrylic, or co-polyester.

8. The lighted suction device of claim 1, wherein the transparent material is glass.

9. A method of suctioning an ear canal of a patient, comprising the steps of:
   a. detachably attaching a light source to the lighted suction device of claim 1,
   b. detachably attaching the lighted suction device of claim 1 to a source of vacuum,
   c. introducing the tip of the lighted suction device of claim 1 into the ear canal of the patient, such that the light transmitted from the light source down the light pipe of the lighted suction device is directed into the ear canal of the patient, providing illumination, and
   d. using the illumination provided to visualize, suction and remove one or more of wax, debris, and foreign objects from the ear canal of the patient.

10. The lighted suction device of claim 1, wherein the suction channel is integral to the light pipe member.

11. A method of suctioning a body orifice of a patient, comprising:
   providing a lighted suction device comprised of a light pipe member extending from a proximal end to a shoulder to a tip, the light piper member being composed of a transparent material with low haze so as to allow light to travel down the light pipe member from the proximal end toward the tip, and a suction channel integral to the light pipe member or a suction catheter member that is affixed in a permanent fashion to the light pipe member having an opening at the tip of the light pipe member and a connector at its proximal end for connection to a source of vacuum, the shoulder of the light pipe member being proximate the tip and having an abrupt transition that exceeds the critical angle for light transmission through the transparent material, such that light transmitted from the light source exits the light pipe member at the shoulder;
   connecting the proximal end of the light pipe member to a light source;
   connecting the connector of the suction channel or suction catheter member to a source of vacuum;
   introducing the tip of the light pipe member into a body orifice of a patient, such that the light transmitted from the light source down the light pipe member is directed from the shoulder into the body orifice of the patient, providing illumination within the body orifice;
   applying suction through the tip of the light pipe member to one or more of wax, debris, and a foreign object in the body orifice of the patient; and
   withdrawing the light pipe member of the lighted suction device from the body orifice of the patient to remove the wax, debris, and/or foreign object therefrom.

12. The method of suctioning a body orifice of claim 11, further comprising the step of detachably attaching a magnification lens onto the proximal end of the lighted suction device to provide enhanced visualization of the body orifice.

13. The method of claim 11, wherein the suction channel of the lighted suction device is integral to the light pipe member.

* * * * *